(12) United States Patent
Sasao et al.

(10) Patent No.: US 8,088,179 B2
(45) Date of Patent: Jan. 3, 2012

(54) HAIR COSMETIC COMPOSITION

(75) Inventors: Yuki Sasao, Aichi-ken (JP); Yasue Yamazaki, Aichi-ken (JP)

(73) Assignee: Hoyu Co., Ltd., Aichi-Ken (JP)

( * ) Notice: Subject to any disclaimer, the term of this patent is extended or adjusted under 35 U.S.C. 154(b) by 0 days.

(21) Appl. No.: 13/131,466

(22) PCT Filed: May 28, 2010

(86) PCT No.: PCT/JP2010/059080
§ 371 (c)(1),
(2), (4) Date: May 26, 2011

(87) PCT Pub. No.: WO2010/140544
PCT Pub. Date: Dec. 9, 2010

(65) Prior Publication Data
US 2011/0229425 A1  Sep. 22, 2011

(30) Foreign Application Priority Data
Jun. 1, 2009 (JP) .................. 2009-132585

(51) Int. Cl.
*A61Q 5/10* (2006.01)

(52) U.S. Cl. ............ 8/405; 8/431; 8/435; 8/552; 8/581; 8/632

(58) Field of Classification Search ............. 8/405, 431, 8/435, 552, 581, 632
See application file for complete search history.

(56) References Cited

U.S. PATENT DOCUMENTS
6,036,730 A * 3/2000 Yoshida et al. ............ 8/406

FOREIGN PATENT DOCUMENTS

| | | |
|---|---|---|
| JP | 2003-081791 A | 3/2003 |
| JP | 2004-175748 A | 6/2004 |
| JP | 2005-089307 A | 4/2005 |
| JP | 2005-139133 A | 6/2005 |
| JP | 2007-326812 A | 12/2007 |
| WO | 2008/096497 A1 | 8/2008 |

* cited by examiner

*Primary Examiner* — Eisa Elhilo
(74) *Attorney, Agent, or Firm* — Seager, Tufte & Wickhem LLC

(57) ABSTRACT

A hair cosmetic composition used for dyeing, bleaching, or destaining hair contains amino-modified silicone, dimethicone, and polyethylene glycol having a number average molecular weight of 10,000 or more.

4 Claims, No Drawings

HAIR COSMETIC COMPOSITION

TECHNICAL FIELD

The present invention relates to a hair cosmetic composition used for dyeing, bleaching, or destaining hair.

BACKGROUND ART

Generally, a hair cosmetic composition used for dyeing, bleaching, or destaining hair contains an alkaline agent and an oxidizing agent. The oxidizing agent acts to remove melanin from hair. The alkaline agent acts to improve lightness of bleached hair by promoting the action of the oxidizing agent. When a hair cosmetic composition contains a dye, the alkaline agent also acts to improve the dyeability of hair by swelling hair so as to improve the permeability of the dye into the hair. A surfactant, an oil component, or a polymer may be added to a hair cosmetic composition. In that case, a certain viscosity is imparted to the hair cosmetic composition, by which dripping is prevented and the adherability of the composition to hair is improved.

Patent Document 1 discloses a hair dye composition containing a cationic surfactant, a nonionic surfactant, a higher alcohol, and amino-modified silicone. The hair dye composition of Patent Document 1 is designed to improve the adherability to hair by using the composition in the form of emulsion. Patent Document 2 discloses a hair cosmetic composition used for bleaching or dyeing hair containing amino-modified silicone, highly polymerized silicone, and a cationic polymer. The hair cosmetic composition of Patent Document 2 is designed to improve the adherability to hair and the feel of the hair treated with the composition by the action of a polymer component having a high molecular weight.

PRIOR ART DOCUMENTS

Patent Document 1: Japanese Laid-Open Patent Publication No. 2005-139133
Patent Document 2: Japanese Laid-Open Patent Publication No. 2004-175748

SUMMARY OF INVENTION

Technical Problem to be Solved by the Invention

However, when using the hair dye composition disclosed in Patent Document 1, in some cases dripping occurs during application to hair due to decreased emulsion stability. With regard to the hair cosmetic composition disclosed in Patent Document 2, it may be possible to, for example, increase the content of a polymer component in order to improve the feel of damaged hair. However, in that case, uniform application to hair becomes difficult due to high viscosity, and as a result, in some cases the hair cannot be evenly bleached or destained.

The present inventors have conducted intensive research. As a result, they have found that the aforementioned problems can be solved by using specific polyethylene glycol and specific silicone in combination, based on which the present invention was completed. An objective of the present invention is to prevent dripping during application of a hair cosmetic composition to hair and to enable uniform dyeing, bleaching, or destaining of hair with the hair cosmetic composition.

Means for solving the Problems

In order to achieve the aforementioned objective, and in accordance with one aspect of the present invention, a hair cosmetic composition used for dyeing, bleaching, or destaining hair is provided that contains amino-modified silicone, dimethicone, and polyethylene glycol having a number average molecular weight of 10,000 or more.

Dimethicone used has a kinematic viscosity of preferably 50,000 mm$^2$/s or less at 25° C.

The number average molecular weight of polyethylene glycol used is preferably 20,000 or more.

Preferably, the hair cosmetic composition contains 0.0025 to 5% by mass, 0.0025 to 5% by mass, and 0.0005 to 5% by mass of the aforementioned amino-modified silicone, dimethicone, and polyethylene glycol, respectively.

EFFECTS OF THE INVENTION

According to the present invention, dripping during application of a hair cosmetic composition to hair can be prevented, and the hair can be evenly dyed, bleached, or destained with the hair cosmetic composition.

MODE FOR CARRYING OUT THE INVENTION

First Embodiment

Hereinbelow, a first embodiment, in which the present invention is embodied as a first, a second, and a third cosmetic composition used for bleaching or destaining hair, will be described.
(First Hair Cosmetic Composition)
The first hair cosmetic composition is a two-part type composed of a first and a second agent, which are mixed upon application, used for bleaching or destaining hair. The first agent contains amino-modified silicone, dimethicone, polyethylene glycol, and an alkaline agent. The second agent contains an oxidizing agent.
(First Agent of First Hair Cosmetic Composition)
Amino-modified silicone, dimethicone, and polyethylene glycol contained in the first agent each act to prevent dripping of the first hair cosmetic composition during application to hair, while enabling uniform bleaching or destaining of the hair by the first hair cosmetic composition, when used in combination. The amino-modified silicone also acts to improve the feel of the hair treated with the first hair cosmetic composition.

The amino-modified silicone used is expressed by the following general formula (1), which is an organosiloxane polymer having at least one aminoalkyl group per molecule.

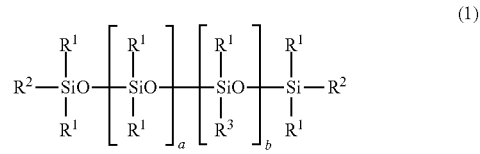

(1)

In the general formula (1), $R^1$ represents a methyl or a hydroxyl group, $R^2$ represents a methyl or a hydroxyl group or $R^3$, $R^3$ represents a substitution group having an amino or an ammonium group represented by $R^4Z$, and "a" and "b" each represent an integer of 1 or greater. $R^4$ represents a divalent hydrocarbon group having a carbon number of 3 to 6. Z represents a monovalent group selected from the group consisting of $-NR^5{}_2$, $-N^+R^5{}_3A^-$, $-NR^5(CH_2)_cNR^5{}_2$, $-NR^5(CH_2)_cN^+R^5{}_3A^-$, and $-NR^5(CH_2)_cNR^5C\!=\!O(R^6)$. $R^5$ represents a hydrogen atom or a hydrocarbon group having a carbon number of 1 to 4, $R^6$ represents a hydrocarbon group having a carbon number of 1 to 4, "A" represents a halogen atom, and "c" represents an integer of 2 to 6.

Specific examples of the amino-modified silicone represented by the general formula (1) include an aminopropylmethylsiloxane-dimethylsiloxane copolymer (aminopropyldimethicone), an aminoethylaminopropylsiloxane-dimethylsiloxane copolymer (amodimethicone), and an aminoethylaminopropylmethylsiloxane-dimethylsiloxane copolymer (trimethylsilylamodimethicone). Only one amino-modified silicone may be used, or two or more amino-modified silicones may be used in combination. Among them, at least one selected from an aminopropylmethylsiloxane-dimethylsiloxane copolymer and an aminoethylaminopropylsiloxane-dimethylsiloxane copolymer is preferably used since the above copolymers have an excellent improving effect on the feel of the hair treated with the first hair cosmetic composition. Of these, an aminoethylaminopropylsiloxane-dimethylsiloxane copolymer is particularly preferably used. The amino-modified silicone used may be a commercially available product. Examples of the commercially available aminoethylaminopropylsiloxane-dimethylsiloxane copolymer include KF-8004 manufactured by Shin-Etsu Chemical Co., Ltd. and XF42-1989 manufactured by Momentive Performance Materials Japan.

The amino-modified silicone content in a mixture of the first and second agents is preferably 0.0025 to 5% by mass, more preferably 0.005 to 2.5% by mass, and further preferably 0.025 to 1% by mass. When the amino-modified silicone content is 0.0025% by mass or more, the feel of the hair treated with the first hair cosmetic composition is particularly improved. When the amino-modified silicone content is 5% by mass or less, dripping during application of the first hair cosmetic composition to hair is well prevented, and the uniformity of bleaching or destaining of hair by the first hair cosmetic composition is improved.

Dimethicone is the INCI name for methylpolysiloxane. Although no particular limitation is imposed on the kinematic viscosity of dimethicone used, the kinematic viscosity at 25° C. is preferably 50,000 mm$^2$/s or less, more preferably 20,000 mm$^2$/s or less, further preferably 10,000 mm$^2$/s or less, and particularly preferably 3,000 mm$^2$/s or less. When the kinematic viscosity of dimethicone used is 50,000 mm$^2$/s or less, the feel of the hair treated with the first hair cosmetic composition is particularly improved, and the uniformity of bleaching or destaining of hair by the first hair cosmetic composition is also improved. The kinematic viscosity of dimethicone varies depending on the polymerization degree of dimethicone. The kinematic viscosity is measured using, for example, an Uberode viscometer in accordance with JIS Z8803 (viscosity of liquid—methods of measurement).

The dimethicone content in a mixture of the first and second agents is preferably 0.0025 to 5% by mass, more preferably 0.005 to 2.5% by mass, and further preferably 0.025 to 1% by mass. When the dimethicone content is somewhere within the above ranges, dripping during application of the first hair cosmetic composition to hair is well prevented, and the uniformity of bleaching or destaining of hair by the first hair cosmetic composition is improved.

The number average molecular weight of polyethylene glycol used must be 10,000 or more, and is preferably 20,000 or more, and more preferably 30,000 or more. When polyethylene glycol having a number average molecular weight of less than 10,000 is used, dripping during application of the first hair cosmetic composition to hair is not sufficiently prevented, and also the uniformity of bleaching or destaining of hair by the first hair cosmetic composition is impaired. The upper limit of the number average molecular weight of polyethylene glycol used is preferably 5,000,000, although no particular limitation is imposed thereon. When polyethylene glycol having a number average molecular weight of 5,000,000 or less is used, the production cost of the first hair cosmetic composition is kept low.

The polyethylene glycol content in a mixture of the first and second agents is preferably 0.0005 to 5% by mass, more preferably 0.005 to 2.5% by mass, and further preferably 0.025 to 1% by mass. When the polyethylene glycol content is somewhere within the above ranges, dripping during application of the first hair cosmetic composition to hair is well prevented. When the polyethylene glycol content is 0.0005% by mass or more, the uniformity of bleaching or destaining of hair by the first hair cosmetic composition is also improved.

An alkaline agent contained in the first agent acts to bleach or destain hair by promoting the action of an oxidizing agent contained in the second agent. Examples of the alkaline agent used include ammonia, alkanolamine, organic amine, inorganic alkali, a basic amino acid, and a salt of these substances. Specific examples of the alkanolamine include monoethanolamine and triethanolamine. Specific examples of the organic amine include 2-amino-2-methyl-1-propanol (AMP), 2-amino-2-methyl-1,3-propanediol, and guanidine. Specific examples of the inorganic alkali include sodium hydroxide, potassium hydroxide, sodium carbonate, and potassium carbonate. Specific examples of the basic amino acid include arginine and lysine. Specific examples of the salt include an ammonium salt. Only one kind of alkaline agent may be used, or two or more kinds thereof may be used in combination. When at least one of alkanolamine and ammonia is used as the alkaline agent, the effect of bleaching or destaining of hair by the first hair cosmetic composition is improved.

The alkaline agent is contained in the first agent in such an amount that the pH of the first agent is preferably within a range of 8 to 12. When the pH of the first agent is 8 or higher, the action of the oxidizing agent contained in the second agent is sufficiently promoted upon mixing of the first and second agents. When the pH of the first agent is 12 or lower, hair is less likely to be damaged by the first hair cosmetic composition.

The first agent may contain a component other than the aforementioned components, for example, water, a water-soluble polymer compound, an additional oil component, an additional polyhydric alcohol, a surfactant, sugar, a preservative, a stabilizing agent, a pH adjuster, a plant extract, a crude drug extract, a vitamin, a fragrance, an anti-oxidant, an ultraviolet ray-absorber, a chelating agent, and an oxidizing aid, as needed.

Water acts as, for example, a solvent.

As the water-soluble polymer compound, any of anionic, cationic, nonionic, and amphoteric ones may be used and any of natural compounds and synthetic compounds may be used. For example, hydroxyethyl cellulose, which is a nonionic synthetic polymer compound, may be used.

The oil component acts to moisturize hair. Specific examples of the oil component include oil/fat, wax, a higher alcohol, a hydrocarbon, a higher fatty acid, an alkylglyceryl ether, an ester, and silicone.

Specific examples of the oil/fat include lanolin, olive oil, camellia oil, shea butter, almond oil, safflower oil, sunflower oil, soybean oil, cottonseed oil, sesame oil, corn oil, rapeseed oil, rice bran oil, rice germ oil, grape seed oil, avocado oil, macadamia nut oil, castor oil, coconut oil, and evening primrose oil. Specific examples of the wax include beeswax, candelilla wax, carnauba wax, jojoba oil, and lanolin. Specific examples of the higher alcohol include cetyl alcohol (cetanol), 2-hexyldecanol, stearyl alcohol, isostearyl alcohol, cetostearyl alcohol, oleyl alcohol, arachyl alcohol, behenyl alcohol, 2-octyldodecanol, lauryl alcohol, myristyl alcohol, decyltetradecanol, and lanolin alcohol.

Specific examples of the hydrocarbon include paraffin, an olefin oligomer, polyisobutene, hydrogenated polyisobutene, mineral oil, squalane, polybutene, polyethylene, microcrystalline wax, and petrolatum. Specific examples of the higher fatty acid include lauric acid, myristic acid, palmitic acid, stearic acid, behenic acid, isostearic acid, 12-hydroxystearic acid, oleic acid, and a lanolin fatty acid. Specific examples of the alkylglyceryl ether include batyl alcohol, chimyl alcohol, serachyl alcohol, and isostearyl glyceryl ether.

Specific examples of the ester include diisopropyl adipate, isopropyl myristate, cetyl octanoate, isononyl isononanoate, octyldodecyl myristate, isopropyl palmitate, stearyl stearate, myristyl myristate, isotridecyl myristate, 2-ethylhexyl palmitate, octyldodecyl ricinoleate, a cholesteryl/lanosteryl fatty acid having a carbon number of 10 to 30, cetyl lactate, acetylated lanolin, ethylene glycol di-2-ethylhexanoate, a pentaerythritol fatty acid ester, a dipentaerythritol fatty acid ester, cetyl caprate, glyceryl tricaprate, diisostearyl malate, dioctyl succinate, and cetyl 2-ethylhexanoate.

Specific examples of the silicone include methylphenylpolysiloxane, decamethylcyclopentasiloxane, dodecamethylcyclohexasiloxane, terminal hydroxyl group-modified dimethylpolysiloxane, polyether-modified silicone, betaine-modified silicone, alkyl-modified silicone, alkoxy-modified silicone, mercapto-modified silicone, carboxyl-modified silicone, and fluorine-modified silicone.

Only one kind of oil component may be used, or two or more kinds thereof may be used in combination.

Specific examples of the polyhydric alcohol include a glycol compound and a glycerin compound. Specific examples of the glycol compound include ethylene glycol, diethylene glycol, triethylene glycol, polyethylene glycol having a number average molecular weight of less than 10,000, propylene glycol, dipropylene glycol, isoprene glycol, and 1,3-butylene glycol. Specific examples of the glycerin compound include glycerin, diglycerin, and polyglycerin.

The surfactant acts as an emulsifying agent or a solubilizing agent, and is used for adjusting the viscosity or improving the viscosity stability. As the surfactant, any of anionic, cationic, amphoteric, and nonionic surfactants may be used.

Specific examples of the anionic surfactant include alkyl ether sulfate, alkyl sulfate, alkenyl ether sulfate, alkenyl sulfate, olefin sulfonate, alkanesulfonate, a saturated or unsaturated fatty acid salt, alkyl or alkenyl ether carbonate, an α-sulfofatty acid salt, an N-acylamino acid type surfactant, a phosphate mono- or di-ester type surfactant, and a sulfosuccinate ester. A counterion for the anionic group of these surfactants may be, for example, any of a sodium ion, a potassium ion, and triethanolamine. For example, sodium lauryl sulfate, which is alkyl sulfate, may be used as the surfactant.

Specific examples of the cationic surfactant include lauryltrimethylammonium chloride, cetyltrimethylammonium chloride, stearyltrimethylammonium chloride, alkyltrimethylammonium chloride, distearyldimethylammonium chloride, cetyltrimethylammonium bromide, stearyltrimethylammonium bromide, lanolin fatty acid aminopropylethyldimethylammonium ethyl sulfate, stearyltrimethylammonium saccharin, cetyltrimethylammonium saccharin, methacryloyloxyethyltrimethylammonium chloride, and behenyltrimethylammonium methyl sulfate.

Specific examples of the amphoteric surfactant include cocobetaine, lauramidopropyl betaine, cocamidopropyl betaine, sodium lauroamphoacetate, sodium cocoamphoacetate, and laurylbetaine (betaine lauryldimethylamino acetate).

Specific examples of the nonionic surfactant include an ether-type nonionic surfactant and an ester-type nonionic surfactant.

Specific examples of the ether-type nonionic surfactant include polyoxyethylene (hereinafter, referred to as POE) cetyl ether (Ceteth), POE stearyl ether (Steareth), POE behenyl ether, POE oleyl ether (Oleth), POE lauryl ether (Laureth), POE octyldodecyl ether, POE hexyldecyl ether, POE isostearyl ether, POE nonylphenyl ether, and POE octylphenyl ether.

Specific examples of the ester-type nonionic surfactant include POE sorbitan monooleate, POE sorbitan monostearate, POE sorbitan monopalmitate, POE sorbitan monolaurate, POE sorbitan trioleate, POE glyceryl monostearate, POE glyceryl monomyristate, POE sorbitol tetraoleate, POE sorbitol hexastearate, POE sorbitol monolaurate, POE sorbitol beeswax, polyethylene glycol monooleate, polyethylene glycol monostearate, polyethylene glycol monolaurate, lipophilic glyceryl monooleate, lipophilic glyceryl monostearate, self-emulsifying glyceryl monostearate, sorbitan monooleate, sorbitan sesquioleate, sorbitan trioleate, sorbitan monostearate, sorbitan monopalmitate, sorbitan monolaurate, a sucrose fatty acid ester, decaglyceryl monolaurate, decaglyceryl monostearate, decaglyceryl monooleate, and decaglyceryl monomyristate.

Only one kind of surfactant may be used, or two or more kinds thereof may be used in combination.

Specific examples of the sugar include sorbitol and maltose.

Specific examples of the preservative include paraben.

Specific examples of the stabilizer include phenacetin, 8-hydroxyquinoline, acetanilide, sodium pyrophosphate, barbituric acid, uric acid, and tannic acid.

Specific examples of the pH adjuster include lactic acid, levulinic acid, glycolic acid, tartaric acid, malic acid, pyrrolidone carboxylic acid (PCA), succinic acid, citric acid, glutamic acid, and arginine.

Specific examples of the antioxidant include ascorbic acid and sulfite.

Specific examples of the chelating agent include ethylenediaminetetraacetic acid (EDTA), diethylenetriaminepentaacetic acid and salts thereof, and hydroxyethanediphosphonic acid (HEDP) and salts thereof.

Specific examples of the oxidizing aid include persulfate such as ammonium persulfate, potassium persulfate, and sodium persulfate. An oxidizing aid is used to intensify bleaching or destaining of hair by the first hair cosmetic composition.

No particular limitation is imposed on the form of the first agent, and the first agent can be in the form of, for example, any of solid, liquid, gel, foam, and cream. Specific examples of the solid form include powder and a granule. Specific examples of the liquid form include an aqueous solution, a suspension, and an emulsified liquid. When the first agent is in the form of solid, the first agent may further contain a dispersant. Specific examples of the dispersant include a metallic salt of stearic acid such as calcium stearate and magnesium stearate, talc, crystalline cellulose, low-substituted hydroxypropyl cellulose, dextrin, and starch.

(Second Agent of First Hair Cosmetic Composition)

An oxidizing agent contained in the second agent acts to remove melanin from hair. Examples of the oxidizing agent used include hydrogen peroxide, urea peroxide, melamine peroxide, sodium percarbonate, potassium percarbonate, sodium perborate, potassium perborate, ammonium persulfate, sodium peroxide, potassium peroxide, magnesium peroxide, barium peroxide, calcium peroxide, strontium peroxide, a hydrogen peroxide adduct of sulfate, a hydrogen peroxide adduct of phosphate, and a hydrogen peroxide adduct of pyrophosphate.

The content of an oxidizing agent in the second agent is preferably 0.1 to 15.0% by mass, more preferably 2.0 to 9.0% by mass, and further preferably 3.0 to 6.0% by mass. When the oxidizing agent content is 0.1% by mass or more, melanin in hair is sufficiently removed. When the oxidizing agent content is 15.0% by mass or less, hair is less likely to be damaged by the first hair cosmetic composition.

When the second agent contains hydrogen peroxide as the oxidizing agent, a stabilizer improving the stability of hydrogen peroxide, for example, ethyleneglycol phenyl ether (phenoxyethanol), hydroxyethanediphosphonic acid, or a salt thereof is preferably added to the second agent. Specific examples of the hydroxyethanediphosphonate include tetrasodium hydroxyethanediphosphonate and disodium hydroxyethanediphosphonate.

The second agent may further contain a component that is generally contained in a composition used for bleaching or destaining hair as long as it does not block the action of each component of the second agent. For example, the second agent may contain a component that is contained in the aforementioned first agent but other than the alkaline agent.

No particular limitation is imposed on the form of the second agent, and the second agent can be in the form of, for example, any of solid (except for the case in which the oxidizing agent is liquid at a normal temperature), liquid, gel, foam, and cream. Specific examples of the solid form include powder and a granule. Specific examples of the liquid form include an emulsified liquid.

The first and second agents are used for bleaching or destaining hair by mixing both of the agents upon application and applying the necessary amount of the resulting mixture to hair using a comb or a brush.

(Second Hair Cosmetic Composition)

The second hair cosmetic composition is a three-part type composed of a first, a second, and a third agent, which are mixed upon application, used for bleaching or destaining hair.

The first agent of the second hair cosmetic composition has a formulation similar to that of the first agent of the first hair cosmetic composition except that it does not contain amino-modified silicone, dimethicone, and polyethylene glycol, and contains at least an alkaline agent.

The second agent of the second hair cosmetic composition has the same formulation as the second agent of the first hair cosmetic composition, and contains at least an oxidizing agent.

The third agent of the second hair cosmetic composition has the same formulation as the first agent of the first hair cosmetic composition, and is in the form of powder or cream.

(Third Hair Cosmetic Composition)

The third hair cosmetic composition is a one-part type used for bleaching hair. The third hair cosmetic composition is contained in a container, for example an applicator container, and upon application, the composition is ejected from the container and applied to hair. The third hair cosmetic composition contains amino-modified silicone, dimethicone, and polyethylene glycol having a number average molecular weight of 10,000 or more, and preferably further contains an alkaline agent and an oxidizing agent. The third hair cosmetic composition is in the form of powder; therefore, the alkaline agent and the oxidizing agent used are preferably in the form of powder. The third hair cosmetic composition may further contain a component that is generally contained in a composition used for bleaching hair as long as it does not block the action of each component of the third hair cosmetic composition.

According to the first embodiment, the following advantages can be attained.

The first, second, and third hair cosmetic compositions contain amino-modified silicone, dimethicone, and polyethylene glycol having a number average molecular weight of 10,000 or more, thereby capable of preventing dripping during application to hair. Further, by using any of the first, second, and third hair cosmetic compositions, hair can also be evenly bleached or destained, and the feel of the treated hair can also be improved.

When the kinematic viscosity of dimethicone contained in each of the first, second, and third hair cosmetic compositions is 50,000 mm$^2$/s or less at 25° C., the feel of the hair treated with the hair cosmetic composition is particularly improved, and the uniformity of bleaching or destaining of hair by the hair cosmetic composition is also improved.

When the number average molecular weight of polyethylene glycol contained in each of the first, second, and third hair cosmetic compositions is 20,000 or more, the uniformity of bleaching or destaining of hair by the hair cosmetic composition is improved.

The first embodiment may be modified as follows.

Amino-modified silicone, dimethicone, and polyethylene glycol may be contained in any of the agents that make up a multi-part type hair cosmetic composition. For example, although amino-modified silicone, dimethicone, and polyethylene glycol are contained in the first agent of the first hair cosmetic composition, at least some of these components may be contained in the second agent of the first hair cosmetic composition, instead of the first agent. Also, although amino-modified silicone, dimethicone, and polyethylene glycol are contained in the third agent of the second hair cosmetic composition, at least some of these components may be contained in the first or the second agent of the second hair cosmetic composition, instead of the third agent.

Each of the first, second, and third hair cosmetic compositions may be modified to a multi-part type composed of four or more agents.

Second Embodiment

Hereinbelow, a second embodiment, in which the present invention is embodied as a fourth hair cosmetic composition used for dyeing hair, will be described. The fourth hair cosmetic composition is a two-part type composed of a first and a second agent, which are mixed upon application.

The first agent of the fourth hair cosmetic composition contains amino-modified silicone, dimethicone, and polyethylene glycol having a number average molecular weight of 10,000 or more, an alkaline agent, and an oxidizing agent. The second agent of the fourth hair cosmetic composition has the same formulation as the second agent of the first hair cosmetic composition, and contains at least an oxidizing agent.

The oxidation dye contained in the first agent can produce color as induced by oxidative polymerization by the oxidizing agent contained in the second agent. The oxidation dye contains at least a dye intermediate, and may additionally contain a coupler.

Specific examples of the dye intermediate include p-phenylenediamine, toluene-2,5-diamine(paratoluoylenediamine), N-phenyl-p-phenylenediamine, 4,4'-diaminodiphenylamine, p-aminophenol, o-aminophenol, p-methylaminophenol, N,N-bis(2-hydroxyethyl)-p-phenylenediamine, 2-hydroxyethyl-p-phenylenediamine, o-chlor-p-phenylenediamine, 4-amino-m-cresol, 2-amino-4-hydroxyethylamino anisole, 2,4-diaminophenol, and a salt of these substances. Only one kind of dye intermediate may be used, or two or more kinds thereof may be used in combination.

The coupler produces color by binding to the dye intermediate. Specific examples of the coupler include resorcine, 5-amino-o-cresol, m-aminophenol, α-naphthol, 5-(2-hydroxyethylamino)-2-methylphenol, m-phenylenediamine, 2,4-diaminophenoxyethanol, toluene-3,4-diamine, 2,6-diaminopyridine, diphenylamine, N,N-diethyl-m-aminophenol, phenylmethylpyrazolone, and a salt of these substances. Only one kind of coupler may be used, or two or more kinds thereof may be used in combination. An oxidation dye containing a dye intermediate and a coupler is preferably used since the dye is capable of changing the color tone of hair as desired.

The first agent of the fourth hair cosmetic composition may further contain, for example, at least one selected from oxidation dyes listed in "the Japanese Standards of Quasi-drug Ingredients" (published in June 2006, Yakuji Nippo Ltd.) and direct dyes.

No particular limitation is imposed on the form of the first and second agents, and they can be in the form of, for example, any of solid, liquid, gel, foam, and cream. Specific examples of the liquid form include an aqueous solution, a suspension, and an emulsified liquid. The first and second agents are used for dyeing hair by mixing both of the agents upon application and applying the necessary amount of the resulting mixture to hair using a comb or a brush.

According to the second embodiment, the following advantages can be attained.

The fourth hair cosmetic composition contains amino-modified silicone, dimethicone, and polyethylene glycol having a number average molecular weight of 10,000 or more, thereby capable of preventing dripping during application to hair. Further, by using the fourth hair cosmetic composition, hair can also be evenly dyed, and the feel of the treated hair can also be improved.

When the kinematic viscosity of dimethicone contained in the fourth hair cosmetic composition is 50,000 mm$^2$/s or less at 25° C., the feel of the hair treated with the fourth hair cosmetic composition is particularly improved. Further, the uniformity of dyeing of hair by the fourth hair cosmetic composition is also improved.

When the number average molecular weight of polyethylene glycol contained in the fourth hair cosmetic composition is 20,000 or more, the uniformity of dyeing of hair by the fourth hair cosmetic composition is improved.

The second embodiment may be modified as follows.

The fourth hair cosmetic composition may be modified to a three-part type similar to the second hair cosmetic composition or a one-part type similar to the third hair cosmetic composition. Alternatively, the fourth hair cosmetic composition may be modified to a multi-part type composed of four or more agents.

EXAMPLES

Subsequently, the present invention will be further specifically described with Examples and Comparative Examples.

The hair dyes (hair cosmetic compositions) of Examples 1 to 26 and Comparative Examples 1 to 6 were prepared. Each of the hair dyes is a two-part type, in which the first agent has the formulation as shown in Table 1 or 2, and the second agent has a common formulation as shown in Table 3. The unit of the content of each component of a hair dye as shown in Tables 1 to 3 is % by mass. The first and second agents of each of the hair dyes were mixed at a mass ratio of 1:1, and the resulting mixture was applied to a bundle of black human hair using a brush. The hair bundle was left at room temperature (25° C.) for 30 minutes, and then the hair dye adhering to the hair bundle was washed off with water. Furthermore, the hair bundle was shampooed twice and conditioned once. The hair bundle was blow-dried with warm air, and then left for a day. At this time, dripping-preventive effect, level-dyeing properties, and feel were evaluated according to the method described below.

It is to be noted that the amino-modified silicone shown in Tables 1 and 2 is an aminoethylaminopropylsiloxane-dimethylsiloxane copolymer (KF-8004 manufactured by Shin-Etsu Chemical Co., Ltd.), and the polyether-modified silicone shown in Table 1 is PEG-9 dimethicone (KF-6013 manufactured by Shin-Etsu Chemical Co., Ltd.).

(Evaluation Method for Dripping-Preventive Effect)

Ten panelists were asked to apply each of the hair dyes to the hair bundle. The hair dye was rated as "5 (excellent)", "4 (good)", "3 (fair)", "2 (slightly poor)", or "1 (poor)" when the number of panelists who responded that dripping was observed during application was 1 or less, 2 to 3, 4 to 5, 6 to 7, and 8 or more, out of 10, respectively. The results of evaluation are shown in Tables 1 and 2.

(Evaluation Method for Level-Dyeing Properties)

Ten panelists were asked to visually observe the hair bundle dyed with each of the hair dyes under a standard light source, and score the uniformity of color tone of the hair bundle on a 5-point scale, namely excellent (5 points), good (4 points), fair (3 points), slightly poor (2 points), and poor (1 point). The hair dye was rated as "5 (excellent)", "4 (good)", "3 (fair)", "2 (slightly poor)", or "1 (poor)" when the average score was 4.6 or more, 3.6 or more and less than 4.6, 2.6 or more and less than 3.6, 1.6 or more and less than 2.6, and less than 1.6, respectively. The results of evaluation are shown in Tables 1 and 2.

(Evaluation Method for Feel)

Ten panelists were asked to compare the feel of the hair bundle dyed with each of the hair dyes and that of a non-dyed hair bundle. The hair dye was rated as "5 (excellent)", "4 (good)", "3 (fair)", "2 (slightly poor)", or "1 (poor)" when the number of panelists who responded that the dyed hair bundle had a favorable feel was 9 or more, 7 to 8, 5 to 6, 3 to 4, and 2 or less, out of 10, respectively. The results of evaluation are shown in Tables 1 and 2.

TABLE 1

| Mixed components | Examples | | | | | | | | |
| --- | --- | --- | --- | --- | --- | --- | --- | --- | --- |
| | 1 | 2 | 3 | 4 | 5 | 6 | 7 | 8 | 9 |
| Amino-modified silicone | 0.5 | 0.5 | 0.5 | 0.5 | 0.5 | 0.5 | 0.5 | 0.5 | 0.5 |
| Polyether-modified silicone | | | | | | | | | |
| Dimethicone (1,000 mm$^2$/s) | 0.1 | | | | | 0.1 | 0.1 | 0.1 | 0.1 |

TABLE 1-continued

| Mixed components | | | | | | | | | |
|---|---|---|---|---|---|---|---|---|---|
| Dimethicone (5,000 mm²/s) | | 0.1 | | | | | | | |
| Dimethicone (12,500 mm²/s) | | | 0.1 | | | | | | |
| Dimethicone (30,000 mm²/s) | | | | 0.1 | | | | | |
| Dimethicone (1,000,000 mm²/s) | | | | | 0.1 | | | | |
| Polyether-modified silicone | | | | | | 0.1 | | | |
| Polyethylene glycol 10000 (molecular weight: 10,000) | | | | | | | 0.1 | | |
| Polyethylene glycol 20000 (molecular weight: 20,000) | | | | | | | | 0.1 | |
| Polyethylene glycol 35000 (molecular weight: 35,000) | | | | | | | | | 0.1 |
| Polyethylene glycol PEG-9M (molecular weight: 400,000) | | | | | | | | | |
| Polyethylene glycol PEG-90M (molecular weight: 4,000,000) | 0.1 | 0.1 | 0.1 | 0.1 | 0.1 | 0.1 | | | |
| Polyethylene glycol 6000 (molecular weight: 6,000) | | | | | | | | | |
| Cetostearyl alcohol | 6 | 6 | 6 | 6 | 6 | 6 | 6 | 6 | 6 |
| POE (7) Cetyl ether | 2 | 2 | 2 | 2 | 2 | 2 | 2 | 2 | 2 |
| POE (10) Cetyl ether | 4 | 4 | 4 | 4 | 4 | 4 | 4 | 4 | 4 |
| POE (20) Cetyl ether | 3 | 3 | 3 | 3 | 3 | 3 | 3 | 3 | 3 |
| Stearyltrimethylammonium chloride | 0.3 | 0.3 | 0.3 | 0.3 | 0.3 | 0.3 | 0.3 | 0.3 | 0.3 |
| Hydroxyethyl cellulose | 0.3 | 0.3 | 0.3 | 0.3 | 0.3 | 0.3 | 0.3 | 0.3 | 0.3 |
| Glycerin | 2 | 2 | 2 | 2 | 2 | 2 | 2 | 2 | 2 |
| Light liquid isoparaffin | 2 | 2 | 2 | 2 | 2 | 2 | 2 | 2 | 2 |
| Sodium sulfite | 0.1 | 0.1 | 0.1 | 0.1 | 0.1 | 0.1 | 0.1 | 0.1 | 0.1 |
| Hydroxyethanediphosphonic acid | 0.1 | 0.1 | 0.1 | 0.1 | 0.1 | 0.1 | 0.1 | 0.1 | 0.1 |
| Fragrance | 0.1 | 0.1 | 0.1 | 0.1 | 0.1 | 0.1 | 0.1 | 0.1 | 0.1 |
| L-Ascorbic acid | 0.3 | 0.3 | 0.3 | 0.3 | 0.3 | 0.3 | 0.3 | 0.3 | 0.3 |
| p-Phenylenediamine | 0.4 | 0.4 | 0.4 | 0.4 | 0.4 | 0.4 | 0.4 | 0.4 | 0.4 |
| p-Aminophenol | 0.6 | 0.6 | 0.6 | 0.6 | 0.6 | 0.6 | 0.6 | 0.6 | 0.6 |
| m-Aminophenol | 0.15 | 0.15 | 0.15 | 0.15 | 0.15 | 0.15 | 0.15 | 0.15 | 0.15 |
| 5-Amino-orthocresol | 0.15 | 0.15 | 0.15 | 0.15 | 0.15 | 0.15 | 0.15 | 0.15 | 0.15 |
| 2,4-Diaminophenoxyethanol | 0.05 | 0.05 | 0.05 | 0.05 | 0.05 | 0.05 | 0.05 | 0.05 | 0.05 |
| 28% Ammonia water | 5 | 5 | 5 | 5 | 5 | 5 | 5 | 5 | 5 |
| Monoethanolamine | 1 | 1 | 1 | 1 | 1 | 1 | 1 | 1 | 1 |
| Purified water | Balance | Balance | Balance | Balance | Balance | Balance | Balance | Balance | Balance |
| Total | 100 | 100 | 100 | 100 | 100 | 100 | 100 | 100 | 100 |
| Evaluation | | | | | | | | | |
| Dripping prevention | 5 | 5 | 5 | 5 | 5 | 5 | 5 | 5 | 5 |
| Level-dyeing properties | 5 | 5 | 4 | 4 | 3 | 5 | 4 | 5 | 5 |
| Feel | 5 | 5 | 5 | 4 | 4 | 5 | 5 | 5 | 5 |

|  | Examples | | Comparative Examples | | | | | |
|---|---|---|---|---|---|---|---|---|
| Mixed components | 10 | 11 | 1 | 2 | 3 | 4 | 5 | 6 |
| Amino-modified silicone | 0.5 | 0.5 | | | 0.5 | 0.5 | 0.5 | 0.5 |
| Polyether-modified silicone | | | | 0.5 | | | | |
| Dimethicone (1,000 mm²/s) | 0.1 | 0.1 | 0.1 | 0.1 | | | 0.1 | 0.1 |
| Dimethicone (5,000 mm²/s) | | | | | | | | |
| Dimethicone (12,500 mm²/s) | | | | | | | | |
| Dimethicone (30,000 mm²/s) | | | | | | | | |
| Dimethicone (1,000,000 mm²/s) | | | | | | | | |
| Polyether-modified silicone | | | | | | 0.1 | | |
| Polyethylene glycol 10000 (molecular weight: 10,000) | | | | | | | | |
| Polyethylene glycol 20000 (molecular weight: 20,000) | | | | | | | | |
| Polyethylene glycol 35000 (molecular weight: 35,000) | | | | | | | | |
| Polyethylene glycol PEG-9M (molecular weight: 400,000) | 0.1 | | | | | | | |
| Polyethylene glycol PEG-90M (molecular weight: 4,000,000) | | | 0.1 | 0.1 | 0.1 | 0.1 | 0.1 | |
| Polyethylene glycol 6000 (molecular weight: 6,000) | | 0.1 | | | | | | 0.1 |
| Cetostearyl alcohol | 6 | 6 | 6 | 6 | 6 | 6 | 6 | 6 |
| POE (7) Cetyl ether | 2 | 2 | 2 | 2 | 2 | 2 | 2 | 2 |
| POE (10) Cetyl ether | 4 | 4 | 4 | 4 | 4 | 4 | 4 | 4 |
| POE (20) Cetyl ether | 3 | 3 | 3 | 3 | 3 | 3 | 3 | 3 |
| Stearyltrimethylammonium chloride | 0.3 | 0.3 | 0.3 | 0.3 | 0.3 | 0.3 | 0.3 | 0.3 |
| Hydroxyethyl cellulose | 0.3 | 0.3 | 0.3 | 0.3 | 0.3 | 0.3 | 0.3 | 0.3 |

TABLE 1-continued

| | | | | | | | | |
|---|---|---|---|---|---|---|---|---|
| Glycerin | 2 | 2 | 2 | 2 | 2 | 2 | 2 | 2 |
| Light liquid isoparaffin | 2 | 2 | 2 | 2 | 2 | 2 | 2 | 2 |
| Sodium sulfite | 0.1 | 0.1 | 0.1 | 0.1 | 0.1 | 0.1 | 0.1 | 0.1 |
| Hydroxyethanediphosphonic acid | 0.1 | 0.1 | 0.1 | 0.1 | 0.1 | 0.1 | 0.1 | 0.1 |
| Fragrance | 0.1 | 0.1 | 0.1 | 0.1 | 0.1 | 0.1 | 0.1 | 0.1 |
| L-Ascorbic acid | 0.3 | 0.3 | 0.3 | 0.3 | 0.3 | 0.3 | 0.3 | 0.3 |
| p-Phenylenediamine | 0.4 | 0.4 | 0.4 | 0.4 | 0.4 | 0.4 | 0.4 | 0.4 |
| p-Aminophenol | 0.6 | 0.6 | 0.6 | 0.6 | 0.6 | 0.6 | 0.6 | 0.6 |
| m-Aminophenol | 0.15 | 0.15 | 0.15 | 0.15 | 0.15 | 0.15 | 0.15 | 0.15 |
| 5-Amino-orthocresol | 0.15 | 0.15 | 0.15 | 0.15 | 0.15 | 0.15 | 0.15 | 0.15 |
| 2,4-Diaminophenoxyethanol | 0.05 | 0.05 | 0.05 | 0.05 | 0.05 | 0.05 | 0.05 | 0.05 |
| 28% Ammonia water | 5 | 5 | 5 | 5 | 5 | 5 | 5 | 5 |
| Monoethanolamine | 1 | 1 | 1 | 1 | 1 | 1 | 1 | 1 |
| Purified water | Balance | Balance | Balance | Balance | Balance | Balance | Balance | Balance |
| Total | 100 | 100 | 100 | 100 | 100 | 100 | 100 | 100 |
| Evaluation | | | | | | | | |
| Dripping prevention | 5 | 5 | 1 | 1 | 1 | 1 | 3 | 3 |
| Level-dyeing properties | 5 | 5 | 2 | 2 | 2 | 2 | 1 | 1 |
| Feel | 5 | 5 | 3 | 4 | 5 | 5 | 5 | 5 |

TABLE 2

| | Examples | | | | | | | |
|---|---|---|---|---|---|---|---|---|
| Mixed components | 12 | 13 | 14 | 15 | 16 | 17 | 18 | 19 |
| Amino-modified silicone | 0.01 | 0.1 | 1 | 5 | 10 | 0.5 | 0.5 | 0.5 |
| Dimethicone (1,000 mm$^2$/s) | 0.1 | 0.1 | 0.1 | 0.1 | 0.1 | 0.01 | 0.1 | 1 |
| Polyethylene glycol PEG-90M (molecular weight: 4,000,000) | 0.1 | 0.1 | 0.1 | 0.1 | 0.1 | 0.1 | 0.1 | 0.1 |
| Cetostearyl alcohol | 6 | 6 | 6 | 6 | 6 | 6 | 6 | 6 |
| POE (7) Cetyl ether | 2 | 2 | 2 | 2 | 2 | 2 | 2 | 2 |
| POE (10) Cetyl ether | 4 | 4 | 4 | 4 | 4 | 4 | 4 | 4 |
| POE (20) Cetyl ether | 3 | 3 | 3 | 3 | 3 | 3 | 3 | 3 |
| Stearyltrimethylammonium chloride | 0.3 | 0.3 | 0.3 | 0.3 | 0.3 | 0.3 | 0.3 | 0.3 |
| Hydroxyethyl cellulose | 0.3 | 0.3 | 0.3 | 0.3 | 0.3 | 0.3 | 0.3 | 0.3 |
| Glycerin | 2 | 2 | 2 | 2 | 2 | 2 | 2 | 2 |
| Light liquid isoparaffin | 2 | 2 | 2 | 2 | 2 | 2 | 2 | 2 |
| Sodium sulfite | 0.1 | 0.1 | 0.1 | 0.1 | 0.1 | 0.1 | 0.1 | 0.1 |
| Hydroxyethanediphosphonic acid | 0.1 | 0.1 | 0.1 | 0.1 | 0.1 | 0.1 | 0.1 | 0.1 |
| Fragrance | 0.1 | 0.1 | 0.1 | 0.1 | 0.1 | 0.1 | 0.1 | 0.1 |
| L-Ascorbic acid | 0.3 | 0.3 | 0.3 | 0.3 | 0.3 | 0.3 | 0.3 | 0.3 |
| p-Phenylenediamine | 0.4 | 0.4 | 0.4 | 0.4 | 0.4 | 0.4 | 0.4 | 0.4 |
| p-Aminophenol | 0.6 | 0.6 | 0.6 | 0.6 | 0.6 | 0.6 | 0.6 | 0.6 |
| m-Aminophenol | 0.15 | 0.15 | 0.15 | 0.15 | 0.15 | 0.15 | 0.15 | 0.15 |
| 5-Amino-orthocresol | 0.15 | 0.15 | 0.15 | 0.15 | 0.15 | 0.15 | 0.15 | 0.15 |
| 2,4-Diaminophenoxyethanol | 0.05 | 0.05 | 0.05 | 0.05 | 0.05 | 0.05 | 0.05 | 0.05 |
| 28% Ammonia water | 5 | 5 | 5 | 5 | 5 | 5 | 5 | 5 |
| Monoethanolamine | 1 | 1 | 1 | 1 | 1 | 1 | 1 | 1 |
| Purified water | Balance | Balance | Balance | Balance | Balance | Balance | Balance | Balance |
| Total | 100 | 100 | 100 | 100 | 100 | 100 | 100 | 100 |
| Evaluation | | | | | | | | |
| Dripping prevention | 4 | 5 | 5 | 4 | 3 | 4 | 5 | 5 |
| Level-dyeing properties | 4 | 5 | 5 | 4 | 3 | 4 | 5 | 5 |
| Feel | 3 | 5 | 5 | 5 | 5 | 5 | 5 | 5 |

| | Examples | | | | | | |
|---|---|---|---|---|---|---|---|
| Mixed components | 20 | 21 | 22 | 23 | 24 | 25 | 26 |
| Amino-modified silicone | 0.5 | 0.5 | 0.5 | 0.5 | 0.5 | 0.5 | 0.5 |
| Dimethicone (1,000 mm$^2$/s) | 5 | 10 | 0.1 | 0.1 | 0.1 | 0.1 | 0.1 |
| Polyethylene glycol PEG-90M (molecular weight: 4,000,000) | 0.1 | 0.1 | 0.01 | 0.1 | 1 | 5 | 10 |
| Cetostearyl alcohol | 6 | 6 | 6 | 6 | 6 | 6 | 6 |
| POE (7) Cetyl ether | 2 | 2 | 2 | 2 | 2 | 2 | 2 |
| POE (10) Cetyl ether | 4 | 4 | 4 | 4 | 4 | 4 | 4 |
| POE (20) Cetyl ether | 3 | 3 | 3 | 3 | 3 | 3 | 3 |
| Stearyltrimethylammonium chloride | 0.3 | 0.3 | 0.3 | 0.3 | 0.3 | 0.3 | 0.3 |

TABLE 2-continued

| | | | | | | | |
|---|---|---|---|---|---|---|---|
| Hydroxyethyl cellulose | 0.3 | 0.3 | 0.3 | 0.3 | 0.3 | 0.3 | 0.3 |
| Glycerin | 2 | 2 | 2 | 2 | 2 | 2 | 2 |
| Light liquid isoparaffin | 2 | 2 | 2 | 2 | 2 | 2 | 2 |
| Sodium sulfite | 0.1 | 0.1 | 0.1 | 0.1 | 0.1 | 0.1 | 0.1 |
| Hydroxyethanediphosphonic acid | 0.1 | 0.1 | 0.1 | 0.1 | 0.1 | 0.1 | 0.1 |
| Fragrance | 0.1 | 0.1 | 0.1 | 0.1 | 0.1 | 0.1 | 0.1 |
| L-Ascorbic acid | 0.3 | 0.3 | 0.3 | 0.3 | 0.3 | 0.3 | 0.3 |
| p-Phenylenediamine | 0.4 | 0.4 | 0.4 | 0.4 | 0.4 | 0.4 | 0.4 |
| p-Aminophenol | 0.6 | 0.6 | 0.6 | 0.6 | 0.6 | 0.6 | 0.6 |
| m-Aminophenol | 0.15 | 0.15 | 0.15 | 0.15 | 0.15 | 0.15 | 0.15 |
| 5-Amino-orthocresol | 0.15 | 0.15 | 0.15 | 0.15 | 0.15 | 0.15 | 0.15 |
| 2,4-Diaminophenoxyethanol | 0.05 | 0.05 | 0.05 | 0.05 | 0.05 | 0.05 | 0.05 |
| 28% Ammonia water | 5 | 5 | 5 | 5 | 5 | 5 | 5 |
| Monoethanolamine | 1 | 1 | 1 | 1 | 1 | 1 | 1 |
| Purified water | Balance | Balance | Balance | Balance | Balance | Balance | Balance |
| Total | 100 | 100 | 100 | 100 | 100 | 100 | 100 |
| Evaluation | | | | | | | |
| Dripping prevention | 4 | 3 | 3 | 5 | 5 | 4 | 3 |
| Level-dyeing properties | 4 | 3 | 3 | 5 | 5 | 4 | 4 |
| Feel | 5 | 5 | 5 | 5 | 5 | 5 | 5 |

TABLE 3

<Second agent>

| Components | |
|---|---|
| Cetanol | 3 |
| POE (30) Cetyl ether | 0.6 |
| POE (5,5) Cetyl ether | 0.2 |
| 35% hydrogen peroxide water | 16.6 |
| Purified water | Balance |
| Total | 100 |

As shown in Tables 1 and 2, the hair dyes of Examples 1 to 26 were rated as "3" or higher in any of the evaluation items of dripping-preventive effect, level-dyeing properties, and feel.

In contrast, the dripping-preventive effect and the level-dyeing properties of the hair dye of Comparative Example 1 lacking amino-modified silicone and the hair dye of Comparative Example 2 containing polyether-modified silicone instead of amino-modified silicone were evaluated lower than those of the hair dyes of Examples.

The dripping-preventive effect and the level-dyeing properties of the hair dye of Comparative Example 3 lacking dimethicone and the hair dye of Comparative Example 4 containing polyether-modified silicone instead of dimethicone were evaluated lower than those of the hair dyes of Examples.

The level-dyeing properties of the hair dye of Comparative Example 5 lacking polyethylene glycol and the hair dye of Comparative Example 6 containing polyethylene glycol having a molecular weight of 6,000 were evaluated lower than that of the hair dyes of Examples.

The invention claimed is:

1. A hair cosmetic composition used for dyeing, bleaching, or destaining hair, comprising amino-modified silicone, dimethicone, and polyethylene glycol having a number average molecular weight of 10,000 or more.

2. The hair cosmetic composition according to claim 1, wherein the dimethicone has a kinematic viscosity of 50,000 mm$^2$/s or less at 25° C.

3. The hair cosmetic composition according to claim 1, wherein the number average molecular weight of the polyethylene glycol is 20,000 or more.

4. The hair cosmetic composition according to claim 1, comprising 0.0025 to 5% by mass of the amino-modified silicone, 0.0025 to 5% by mass of the dimethicone, and 0.0005 to 5% by mass of the polyethylene glycol.

* * * * *